United States Patent [19]

Williams

[11] 4,331,468

[45] May 25, 1982

[54] PROCESS FOR INHIBITING FORMATION OF NITROSAMINES

[75] Inventor: Michael L. Williams, Newark, Ohio

[73] Assignee: The Dow Chemical Company, Midland, Mich.

[21] Appl. No.: 256,420

[22] Filed: Apr. 22, 1981

Related U.S. Application Data

[63] Continuation-in-part of Ser. No. 152,459, May 23, 1980, abandoned.

[51] Int. Cl.³ .............................................. E05B 63/14
[52] U.S. Cl. .......................................... 71/121; 564/2; 564/5; 71/98; 71/107; 71/14; 71/118; 71/125
[58] Field of Search ......................... 564/2, 5; 71/121

[56] References Cited

U.S. PATENT DOCUMENTS

| | | | |
|---|---|---|---|
| 2,392,859 | 1/1946 | Meuli | 167/45 |
| 2,509,891 | 5/1950 | Starr et al. | 564/5 |
| 2,745,781 | 5/1956 | Stewart | 167/31 |
| 3,499,931 | 3/1970 | Tindall | 260/584 |
| 3,535,260 | 10/1970 | Singh | 564/2 X |
| 3,567,779 | 3/1971 | Currier et al. | 564/2 |

OTHER PUBLICATIONS

Morrison et al., "Organic Chemistry", 2nd Ed., Boston, Allyn and Bacon, 1966, pp. 743 and 758–759.
Sidgwick, "Organic Chemistry of Nitrogen", 3rd Ed., Clarendon Press, Oxford (1966), pp. 414+595.
Douglas et al., "J. Soc. Cosmet. Chem.", 29, pp. 581–606, 1978.
Keefer et al., "Science", 181 (4106), pp. 1245–1246, 1973.
Sen et al., "J. Agr. Food Chem.", 22 (6), pp. 1125–1130 (1974).
Mirvish et al., "Science", 177 (4043), pp. 65–68, 1972.
Mirvish, "Annals N.Y. Academy of Sciences", 258, pp. 175–180, 1975.
Sen et al., "IARC Sci. Publ.", 9, pp. 103–106, 1975.
Sen et al., "J. Agric. Food Chem.", 24 (2), pp. 397–401, 1976.
Walker et al., "Nature", 258, p. 176, 1975.

*Primary Examiner*—Paul F. Shaver

[57] ABSTRACT

Process for inhibiting formation of nitrosamines in nitro herbicide formulations containing (a) materials having nitrosatable nitrogen functional groups and (b) nitrosating agents or precursors thereof, comprising admixing with one or more ingredients of such formulations, prior to formation of nitrosamines, nitrosamine retarding amounts of at least one monoalkanolamine of the formula:

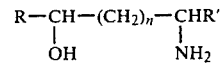

where n is a whole number in the range of 0–5; R and R' are independently H or an alkyl group containing 1–5 carbon atoms; or at least one acid salt of said monoalkanolamines.

7 Claims, No Drawings

PROCESS FOR INHIBITING FORMATION OF NITROSAMINES

CROSS REFERENCE TO RELATED APPLICATION

This application is a continuation-in-part of copending application Ser. No. 152,459 filed May 23, 1980, now abandoned.

BACKGROUND OF THE INVENTION

Undesirable nitrosamines are often found in herbicidal and other compositions or formulations which contain constituents having (a) nitrosatable nitrogen functional groups, such as secondary or tertiary amines, in addition to (b) materials with potential nitrosating activity, such as 2,4-dinitro-6-sec-butylphenol (dinoseb) contaminated with a nitrosating agent or agents, such as HONO or precursors thereof.

For example, contaminating amounts of N-nitrosodiethanolamine (NDELA) can be found in formulations made with alkanolamines, e.g., mixtures of alkanolamines containing triethanolamine and diethanolamine, and technical grades of 2,4-dinitro-6-sec-butylphenol. Such undesirable product is formed by the combination of diethanolamine and/or triethanolamine in the alkanolamine mixture and nitrosating agents or precursors thereof present as impurities in the 2,4-dinitro-6-sec-butylphenol. Typically, there are no significant nitrosamine levels in the technical grade 2,4-dinitro-6-sec-butylphenol or in any of the formulating agents prior to the time the constituents are mixed together.

Since nitrosamines have been reported to cause tumors in rats, compositions or formulations having potential for nitrosamine formation may present the possibility of adverse effects on people involved in the handling and use of such materials. Thus, any means to minimize the formation of nitrosamines in such compositions or formulations is desirable.

SUMMARY OF THE INVENTION

This invention relates to a process for inhibiting formation of nitrosamines in nitro herbicides or other formulations containing (a) materials having nitrosatable nitrogen functional groups and (b) nitrosating agents or precursors thereof, comprising admixing with one or more ingredients of said formulations, prior to formation of nitrosamines, nitrosamine retarding amounts of at least one monoalkanolamine of the formula:

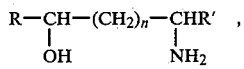

where n is a whole number in the range of 0–5; R and R' are independently H or an alkyl group containing 1–5 carbon atoms; or at least one acid salt of such monoalkanolamines.

The process of this invention has applications in agricultural formulations, in cutting fluids, in cosmetics, and in any other area where secondary and/or tertiary alkanolamines or other nitrosatable materials are used and nitrosamine formation is a potential problem.

This invention is particularly useful with herbicide formulations containing as herbicidally active species one or more organic compounds containing one or more nitro substituents. Such herbicidally active nitro compounds are sometimes contaminated by nitrosating agents or precursors thereof resulting from nitrating processes utilized in making the compounds.

Representative herbicidally active nitro compounds include, for example,

| Common Name | Chemical Name |
|---|---|
| acifluorfen | 5-(2-chloro-4-(trifluoromethyl)-phenoxy)-2-nitrobenzoic acid |
| benefin | N-butyl-N-ethyl-2,6-dinitro-4-(trifluoromethyl)benzenamine |
| bifenox | 5-(2,4-dichlorophenoxy)-2-nitrobenzoic acid methyl ester |
| butralin | 4-(1,1-dimethylethyl)-N-(1-methylpropyl)-2,6-dinitrobenzenamine |
| dinitramine | $N^3,N^3$-diethyl-2,4-dinitro-6-(trifluoromethyl)-1,3-benzenediamine |
| dinoseb | 2,4-dinitro-6-sec-butylphenol |
| ethalfluralin | N-ethyl-N-(2-methyl-2-propenyl)-2,6-dinitro-4-(trifluoromethyl)-benzenamine |
| fluchloralin | N-(2-chloroethyl)-2,6-dinitro-N-propyl-4-(trifluoromethyl)benzenamine |
| isopropalin | 4-(1-methylethyl)-2,6-dinitro-N,N-dipropylbenzenamine |
| nitralin | 4-(methylsulfonyl)-2,6-dinitro-N,N-dipropylbenzenamine |
| nitrofen | 2,4-dichloro-1-(4-nitrophenoxy)-benzene |
| oxyzalin | 4-(dipropylamino)-3,5-dinitrobenzenesulfonamide |
| oxyfluorofen | 2-chloro-1-(3-ethoxy-4-nitrophenoxy)-4-(trifluoromethyl)benzene |
| pendimethalin | N-(1-ethylpropyl)-3,4-dimethyl-2,6-dinitrobenzenamine |
| prodiamine | 2,4-dinitro-$N^3,N^3$-dipropyl-6-(trifluoromethyl)-1,3-benzenediamine |
| profluralin | N-(cyclopropylmethyl)-2,6-dinitro-N-propyl-4-(trifluoromethyl)benzenamine |
| prosulfalin | N-((4-(dipropylamino)-3,5-dinitrophenyl)sulfonyl)-S,S-dimethylsulfilimine |
| trifluralin | 2,6-dinitro-N,N-dipropyl-4-(trifluoromethyl)benzenamine. |

The invention is most advantageously used with formulations containing secondary and/or tertiary alkanolamine salts of 2,4-dinitro-6-sec-butylphenol (as disclosed for example in U.S. Pat. Nos. 2,392,859 and 2,745,781).

DETAILED DESCRIPTION AND EMBODIMENTS

According to this invention, examples of materials which contain moieties which may be nitrosatable nitrogen functional groups include, but are not limited to: secondary alkylamines; tertiary alkylamines; secondary arylamines; tertiary arylamines; secondary alkanolamines; tertiary alkanolamines; primary amides; N-alkylcarbamates; N-arylcarbamates; quaternary ammonium compounds; triazines; N,N,N',N'-tetra-substituted hydrazines; combinations of one or more of the above; and acid salts of the above.

This invention is particularly useful in processes, and compositions, wherein the materials having nitrosatable nitrogen functional groups comprise mixtures of dialkanolamines and trialkanolamines, wherein said mixtures of dialkanolamines and trialkanolamines comprise from 80 to 99.9 weight percent trialkanolamine and from 0.1 to 20 weight percent dialkanolamine.

Nitrosating agents or precursors thereof as contemplated in the broad aspect of this invention include any material capable of nitrosating a nitrosatable nitrogen functional group. Such nitrosating agents include, for example, HONO or precursors thereof, and are generally thought to nitrosate by reaction of the nitrosonium ion +NO with the nitrosatable material. These nitrosating agents or precursors thereof may be contained as impurities in materials which have been prepared using nitration reactions, such as the nitro herbicides, of which 2,4-dinitro-6-sec-butylphenol is an example.

Monoalkanolamines useful in the practice of this invention include compounds of the formula:

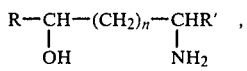

or acid salts thereof, where n is a whole number in the range of 0-5, and R and R' are independently H or an alkyl group containing 1-5 carbon atoms. Representative, but non-limiting examples of monoalkanolamines useful in the practice of this invention include: monoethanolamine (2-aminoethanol); 1-amino-2-propanol; 2-amino-1-propanol; 3-amino-1-propanol; 2-amino-1-butanol, and acid salts thereof.

This invention utilizes the addition of at least one monoalkanolamine or acid salt thereof as defined herein to a material containing a nitrosating agent or agents or precursors thereof, so that the formation of nitrosamines from nitrosatable nitrogen functional groups is reduced.

According to one aspect of this invention, at least one monoalkanolamine or salt thereof is added to a material containing a nitrosatable nitrogen functional group to protect the nitrosatable group from nitrosation by a nitrosating agent or agents or precursors thereof which are added at some subsequent time. For example, at least one monoalkanolamine or salt thereof is added to a formulation containing dialkanolamine and/or trialkanolamine salts of 2,4-dichlorophenoxyacetic acid to reduce nitrosation of the dialkanolamine and/or trialkanolamine moieties by nitrosating agents which are added subsequently, such as when nitrosating agents are present in water of dilution, which is added later. Similarly, at least one monoalkanolamine or acid salt thereof is added to formulations containing ingredients such as 2,4-dichlorophenoxyacetic acid:dialkylamine salts, 4-chloro-2-methylphenoxyacetic acid:dialkanolamine and/or trialkanolamine salts, or 4-amino-3,5,6-trichloropicolinic acid: dialkanolamine and/or trialkanolamine salts.

In another embodiment, the monoalkanolamine or acid salt thereof is added at about the same time as all the other individual ingredients, including materials containing a nitrosating agent or agents or precursors thereof, and one or more nitrosatable nitrogen containing compounds. This embodiment is exemplified by a process in which a monoalkanolamine, one or more secondary and/or tertiary alkanolamines, and 2,4-dinitro-6-sec-butylphenol (contaminated with one or more nitrosating agents or precursors thereof), and inert ingredients such as solvents are mixed together to give a formulation containing alkanolamine salts of 2,4-dinitro-6-sec-butylphenol.

In the most preferred embodiment, the monoalkanolamine or acid salt thereof is added to the material containing the nitrosating agent or agents or precursors thereof and subsequently the material containing the nitrosatable nitrogen functional group is added. For example, a monoalkanolamine is added to pretreat a 2,4-dinitro-6-sec-butylphenol material which contains one or more nitrosating agents or precursors thereof as impurities, and dialkanolamine and/or trialkanolamine is subsequently added to give a formulation containing alkanolamine salts of 2,4-dinitro-6-sec-butylphenol.

Typically, the monoalkanolamine or acid salt thereof is added in an amount sufficient to provide a concentration of 0.1 to 4 weight percent of the final formulation, but any effective level can be used.

The following examples illustrate certain specific embodiments of this invention. Unless otherwise indicated, all parts and percentages are by weight.

EXAMPLE 1

Technical grade 2,4-dinitro-6-sec-butylphenol containing nitrosating impurities was premixed with monoethanolamine in methanol and water under reflux at 50° C. for 24 hours. The other formulating ingredients (see Table 1) were added, and the samples were stored at 50° C. for 90 days and samples were analyzed for N-nitrosodiethanolamine content at various times using reverse phase high performance liquid chromatography. The data in Table 1 show the reduced levels of N-nitrosodiethanolamine in samples using monoethanolamine-pretreated 2,4-dinitro-6-sec-butylphenol. The results also show reduced nitrogen oxide levels in monoethanolamine-pretreated technical 2,4-dinitro-6-sec-butylphenol (NOx levels were determined by ion chromatography after the conversion of nitrogen oxides to nitrate and nitrite by treatment with NaOH) suggesting that the monoethanolamine pretreatment of technical 2,4-dinitro-6-sec-butylphenol may reduce N-nitrosodiethanolamine levels by a mechanism involving preferential scavenging of nitrogen oxides.

TABLE 1

| | Formulation Compositions (Parts by Weight) | | | | | | NOx Conc. in Technical Dinoseb | | Resultant NDELA Concentration (ppm) | | |
|---|---|---|---|---|---|---|---|---|---|---|---|
| | Technical Dinoseb | TEA | MEA | DEA | Versenic Acid | Water and Inerts | Methanol | NO$_2$ (ppm) | NO$_3$ (ppm) | 3 day | 30 day | 90 day |
| a | 33 | 19 | — | 5.9 | 2.0 | 22.2 | 18 | 1400 | 300 | 124 | 420 | NA |
| b | 33 | 19 | 1.6 | 5.9 | 2.0 | 22.2 | 18 | <200 | <200 | 6 | 34 | 125 |
| c | 33 | 19 | 2.7 | 3.4 | 1.4 | 19.7 | 17 | <200 | <200 | 4 | 19 | 132 |

Dinoseb = 2,4-dinitro-6-sec-butylphenol
TEA = triethanolamine
DEA = diethanolamine
MEA = monoethanolamine
NDELA = N-nitrosodiethanolamine
NA = Not available

EXAMPLE 2

Direct addition of monoethanolamine to the final formulation of technical grade 2,4-dinitro-6-sec-butylphenol (i.e., where the technical grade 2,4-dinitro-6-sec-butylphenol is not pretreated with monoethanolamine prior to the addition of other formulating ingredients) is also effective in reducing formation of N-nitrosodiethanolamine. In this example, all formulating ingredients, including monoethanolamine, were added at one time. The samples were stored at 50° C. for 72 hours and analyzed for N-nitrosodiethanolamine content using reverse phase high performance liquid chromatography. The pH of each formulation was also measured.

The data of Table 2 show the decreased levels of N-nitrosodiethanolamine in the presence of monoethanolamine.

TABLE 2

| | Technical Dinoseb | TEA | DEA | MEA | Versenic Acid | Water and Inerts | Methanol | Resultant NDELA Conc. (ppm) | pH |
|---|---|---|---|---|---|---|---|---|---|
| a | 33 | 19 | 5.9 | — | 2.0 | 23.2 | 17 | 124 | 8.56 |
| b | 33 | 19 | 5.9 | 1.6 | 2.0 | 23.2 | 16 | 38 | 8.53 |
| c | 33 | 19 | 3.3 | 2.7 | 1.3 | 25.8 | 15 | 21 | 8.73 |

Dinoseb = 2,4-dinitro-6-sec-butylphenol
TEA = triethanolamine
DEA = diethanolamine
MEA = monoethanolamine
NDELA = N-nitrosodiethanolamine

EXAMPLE 3

Formulations having reduced levels of diethanolamine present were made. Monoethanolamine was added to the formulations, the samples were stored at 50° C. for 72 hours and analyzed for N-nitrosodiethanolamine content using reverse phase high performance liquid chromatography. The data of Table 3 demonstrate the reduction of N-nitrosodiethanolamine levels by reducing the amount of diethanolamine present in the formulation and a further reduction by the addition of monoethanolamine (without pretreatment of the 2,4-dinitro-6-sec-butylphenol).

TABLE 3

| | Technical Dinoseb | TEA | DEA | MEA | Versenic Acid | Water and Inerts | Methanol | Resultant NDELA Conc. (ppm) |
|---|---|---|---|---|---|---|---|---|
| a | 33 | 19 | 6.5 | — | 2.0 | 22.2 | 17 | 124 |
| b | 32 | 22 | 2.6 | — | 2.0 | 28.1 | 15 | 14 |
| c | 32 | 22 | 2.6 | 2.0 | 2.0 | 26.1 | 15 | 5 |
| d | 32 | 18 | 0.01 | 3.1 | 2.0 | 28.7 | 15 | 2 |

Dinoseb = 2,4-dinitro-6-sec-butylphenol
TEA = triethanolamine
DEA = diethanolamine
MEA = monoethanolamine
NDELA = N-nitrosodiethanolamine Similarly, experiments with formulations containing low levels of diethanolamine and containing 2,4-dinitro-6-sec-butylphenol which has been pretreated with monoethanolamine also show markedly reduced levels of N-nitrosodiethanolamine.

What is claimed is:

1. A process for inhibiting formation of nitrosamines in nitro herbicide formulations containing (a) materials having nitrosatable nitrogen functional groups and (b) nitrosating agents or precursors thereof, which comprise admixing with one or more ingredients of such formulations, prior to the formation of said nitrosamines, a nitrosamine retarding amount of at least one monoalkanolamine having the formula

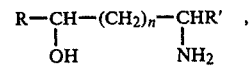

where n is a whole number in the range from 0 to 5; R and R' are independently H or an alkyl group containing 1–5 carbon atoms; or at least one acid salt of said monoalkanolamines.

2. The process of claim 1 wherein the monoalkanolamine or acid salt thereof is present in an amount sufficient to provide a concentration of from 0.1 to 4 weight percent based on the total weight of the formulation.

3. The process of claim 2 wherein the material having nitrosatable nitrogen functional groups is a mixture of secondary and tertiary ethanolamines.

4. The process of claim 3 wherein the mixture of secondary and tertiary ethanolamines comprises from about 80 to about 99.9 weight percent triethanolamine and from about 0.1 to about 20 weight percent of diethanolamine.

5. The process of claim 4 wherein the nitrosating agent or precursor thereof is an impurity in 2,4-dinitro-6-sec-butylphenol.

6. The process of claim 5 wherein the monoalkanolamine is monoethanolamine.

7. The process of claim 1 wherein the nitrosating agent or precursor thereof is treated with the monoalkanolamine or salt thereof prior to admixture with the material having nitrosatable nitrogen functional groups.

* * * * *